United States Patent [19]

Devocelle et al.

[11] Patent Number: 5,434,258
[45] Date of Patent: Jul. 18, 1995

[54] $\delta^{1,4}$-PREGNADIENE-3,20-DIONES

[75] Inventors: Luc Devocelle, Saint Gratien; Philippe Mackiewicz, Livry Gargan, both of France

[73] Assignee: Roussel Uclaf, France

[21] Appl. No.: 190,881

[22] Filed: Feb. 2, 1994

Related U.S. Application Data

[62] Division of Ser. No. 974,484, Nov. 12, 1992, Pat. No. 5,310,896, which is a division of Ser. No. 856,546, Mar. 24, 1992, abandoned.

[30] Foreign Application Priority Data

Apr. 10, 1991 [FR] France .................. 91 04339

[51] Int. Cl.⁶ ............................................. C07J 75/00
[52] U.S. Cl. .......................................... 540/63; 552/566
[58] Field of Search ................... 540/27, 17, 63; 514/172

[56] References Cited

U.S. PATENT DOCUMENTS 5,053,404 10/1991 Molnar et al. .................. 540/27
5,310,896 5/1994 Devocelle et al. ................ 540/63

*Primary Examiner*—Nicholas Rizzo
*Attorney, Agent, or Firm*—Bierman and Muserlian

[57] ABSTRACT

A compound of the formula

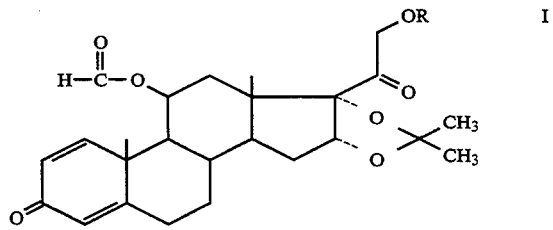

wherein R is selected from the group consisting of hydrogen, acyl of an organic carboxylic acid of 1 to 8 carbon atoms, allyloxycarbonyl, alkoxycarbonyl and aralkoxycarbonyl of up to 8 carbon atoms and alkylsulfonyl and arylsulfonyl of up to 8 carbon atoms and their use to prepare substituted 16,17-methylenedioxy-steroids and novel intermediates.

1 Claim, No Drawings

$\Delta^{1,4}$-PREGNADIENE-3,20-DIONES

This is a division of Ser. No. 974,484 filed Nov. 12, 1992, now U.S. Pat. No. 5,310,896 which is a division of U.S. patent application Ser. No. 856,546 filed Mar. 24, 1992, now abandoned.

OBJECTS OF THE INVENTION

It is an object of the invention to provide the novel steroids of formula I and a novel process and intermediates for their preparation.

It is another object of the invention to provide novel processes for the preparation of substituted 16,17-methylenedioxy-steroids.

These and other objects and advantages of the invention will become obvious from the following detailed description.

THE INVENTION

The novel $\Delta^{1,4}$-pregnadienes of the invention have the formula

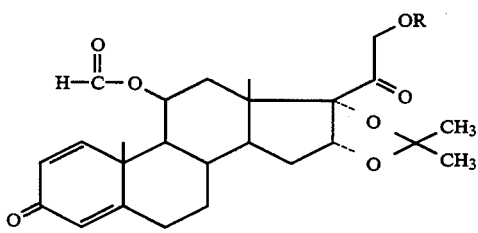

wherein R is selected from the group consisting of hydrogen, acyl of an organic carboxylic acid of 1 to 8 carbon atoms, allyloxycarbonyl, alkoxycarbonyl and aralkoxycarbonyl of up to 8 carbon atoms and alkylsulfonyl and arylsulfonyl of up to 8 carbon atoms.

Examples of R as acyl are formyl, acetyl, propionyl, butyryl, pivaloyl and succinyl and as alkoxycarbonyl or aralkoxycarbonyl are benzyloxycarbonyl, tertbutoxycarbonyl, ethoxycarbonyl and methoxycarbonyl. Examples of R as alkylsulfonyl or arylsulfonyl are methylsulfonyl, phenylsulfonyl and tolylsulfonyl.

R is preferably acyl of an organic carboxylic acid of 1 to 8 carbon atoms and a specific preferred compound of formula I is (11$\beta$,16$\alpha$) 11-formyloxy-16,17-[(1-methylethylidene)-bis oxy]-21-acetyloxy-$\Delta^{1,4}$-pregnadiene-3,20-dione.

The process of the invention for the preparation of a compound of formula I comprises reacting a compound of the formula

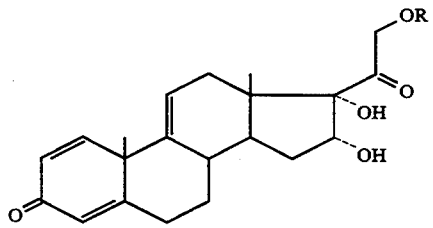

wherein R has the above definition with a chlorination or bromination agent and a formyloxylation agent in an acid medium to obtain a compound of the formula

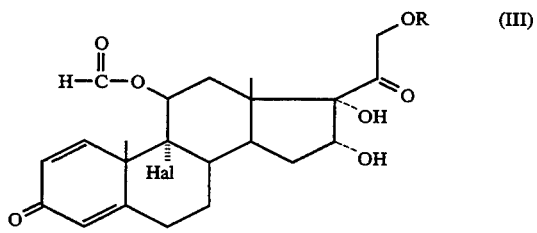

wherein R is defined as above and Hal is chlorine or bromine, reacting the latter with acetone in the presence of a strong acid to obtain a compound of the formula

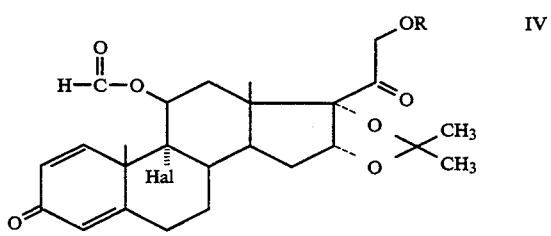

and reacting the latter with a dehalogenation agent to obtain the compound of formula I.

The chlorination or bromination agent is an N-chloro or N-bromo amide and more particularly N-chloro-or N-bromo-acetamide, succinimide or phthalimide or N,N-dichloro or N,N-dibromo-dimethyl hydantoin. It can also be a hypochlorite or a hypobromite, in particular tert-butyl. The formyloxylation agent is preferably dimethylformamide or formic acid.

As indicated above, the operation is carried out in an acid medium. Thus, if dimethylformamide is used, the operation is preferably carried out in the presence of a strong acid such as perchloric acid or fluoroboric acid. If formic acid is used, it is used on its own, or in a buffered medium in the presence of a sodium or potassium formate and, if appropriate, adding an acid such as hydrochloric acid.

The strong acid used during the ketalization can be perchloric acid, fluoroboric acid or also a sulfonic acid, for example methane sulfonic acid, benzene sulfonic acid or p-toluene sulfonic acid, as well as sulfuric acid, hydrochloric acid or hydrobromic acid. Perchloric acid or fluoroboric acid are particularly preferred. The ketalization can be carried out in the presence of a dehydrating agent, particularly in the presence of isopropenyl acetate. Dimethoxypropane, methyl or ethyl orthoformate or a molecular sieve can also be used.

The dehalogenation can be carried out by an organotin hydride such as tributyltin hydride, preferably in the presence of a radical reaction initiator such as azobisisobutyronitrile or benzoyl peroxide. The operation is preferably carried out in an alkanol, for example isopropanol or tert-butanol but can also be carried out in ethyl acetate, acetonitrile, toluene or dimethylformamide.

The dehalogenation can also be carried out by tin (0) or lead (0), or by a salt of tin (II) or lead (II), in the presence of a hydrogen donor such as a thiol like ethanedithiol, propane-1,3-dithiol or butanethiol, mercaptoacetic acid, 3-mercapto-propionic acid or also hypophosphorous acid, and of a radical reaction initiator, such as those mentioned above, particularly in solvent conditions described in the Patent Application No.

WO 90/09394. A derivative of chromium (II) can also be used, notably a chromium (II) salt or carboxylate such as the acetate or stearate in the presence of a hydrogen donor such as those mentioned above in a polar solvent such as dimethylformamide, dimethylsulfoxide or dimethylacetamide. Finally, tris(trimethylsilyl) silane can also be used in the presence of a radical reaction initiator such as those mentioned above.

Also a subject of the invention is the process for the preparation of a compound of the formula

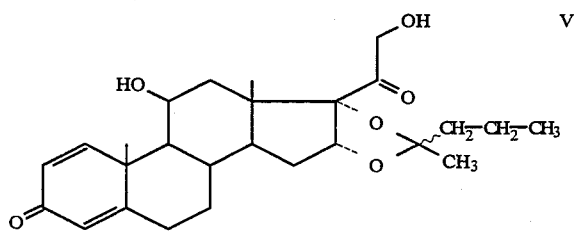

in which the wavy line indicates the existence of two isomers, the compounds appearing in the form of a mixture of these isomers comprising reacting a compound of formula I with butanal in the presence of a strong acid catalyst to obtain a compound of the formula

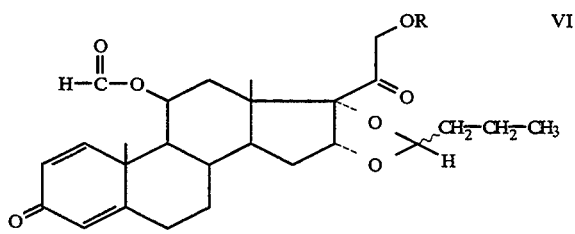

in which R and the wavy line are defined as above and subjecting the latter to a solvolysis in a basic medium to obtain the compound of formula V.

Preferably, R is acetyl and the strong acid used in the reaction with butanal is preferably perchloric acid. Fluoroboric acid can also be used. The operation is carried out in a halogenated solvent, particularly methylene chloride or chloroform, preferably at a temperature of −5° to +10° C.

The solvolysis of the compounds of formula VI is preferably an alcoholysis carried out in the presence of a catalytic quantity of sodium hydroxide or potassium hydroxide. The alcohol is preferably methanol or ethanol and the operation is carried out in a cosolvent which can be dioxane, tetrahydrofuran, or methylene chloride, chloroform or ethyl acetate. Dioxane is particularly preferred. The solvolysis of the compounds of formula VI can also be a hydrolysis using, for example, the bases mentioned above.

According to the invention, it is also possible to prepare the compound of formula V as defined previously, by reacting a compound of formula IV with butanal in the presence of a strong acid catalyst to obtain a compound of the formula

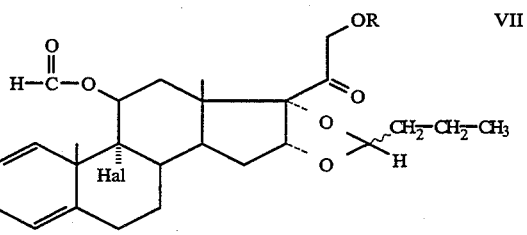

wherein Hal, R and the wavy line are defined as above and reacting the latter with a dehalogenation agent to obtain a compound of formula VI and then the synthesis is continued as described above. The conditions for implementation of this process are the same as those which have been described above for the corresponding reactions.

The process for the preparation of a compound of the formula

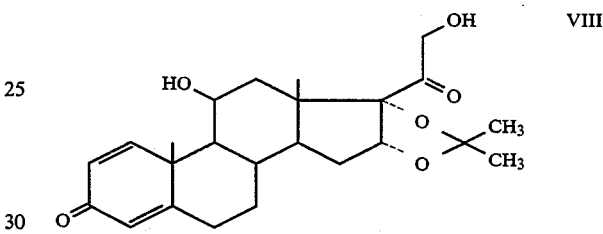

comprises subjecting a compound of formula I to a solvolysis in a basic medium, preferably R is acetyl. The solvolysis of the compounds of formula I is preferably carried out under the conditions set out above, for that of the compounds of formula VI.

The novel industrial compounds of the invention are compounds of the formulae

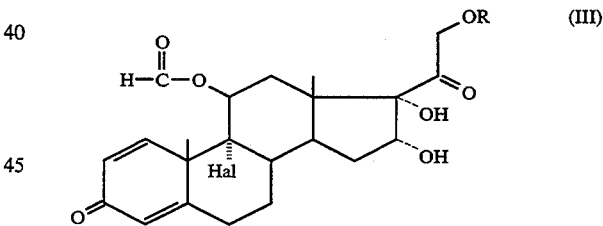

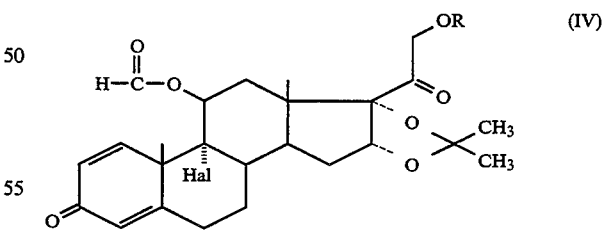

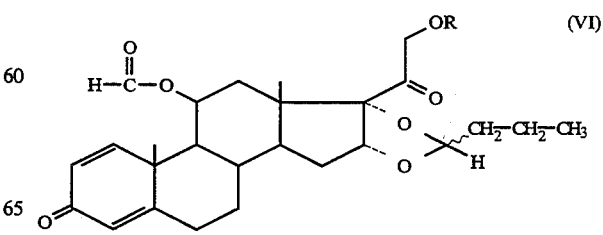

and

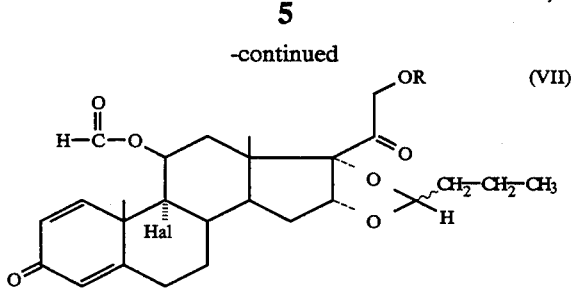

in which Hal and R are defined as above.

The compounds of formulae V and VIII are therapeutically active compounds known in the literature, under the names budesonide and desonide, for example French Patent No. 2,185,405 and U.S. Pat. No. 2,990,401.

The compounds of formula II used at the start of the process of the invention are described for example in U.S. Pat. Nos. 2,998,433; 3,047,468 or can be obtained from intermediate products described in these Patents by methods known to a man skilled in the art.

In the following examples, there are described several preferred embodiments to illustrate the invention.- .However, it is to be understood that the invention is not intended to be limited to the specific embodiments.

EXAMPLE 1

(11$\beta$, 16$\alpha$)-formyloxy)-16,17-[(1-methylethylidene)-bis(oxy)-- 21-(acetyloxy)-$\Delta^{1,4}$-pregnadiene-3,2--dione STEP : (9$\alpha$, 11$\beta$, 16$\alpha$)-21-(acetyloxy)-9-bromo-11-(formyloxy)-$\Delta^{1,4}$-pregnadiene-16,17-diol-3,20-dione 80 g of (16$\alpha$)-21-(acetyloxy)-$\Delta^{1,4,9(11)}$-pregnatriene-16,17diol-3,20-dione and 480 ml of dimethylformamide were mixed together at ambient temperature under inert gas and in the dark and then 42.64 g of N-bromosuccinimide were added to the mixture with stirring at 5° to +10° C. Then, over about 30 minutes and while allowing the temperature to rise to +20° to +22° C., a solution of 42 6 ml of perchloric acid at 55° Be in 107 ml of water was added and after the mixture was stirred at ambient temperature for 3 hours 30 minutes, the mixture was poured into a water-ice mixture. The crystals were separated out, washed with water and dried to obtain 102.3 g of the expected product which was crystallized by dissolution in dimethylformamide, adding water, separating and impasting the crystals in methanol to obtain the product melting at approx. 260° C. (dec.), and having a specific rotation of $[\alpha]_D^{20} = +111.5° \pm 3°$ (c=1% in DMF).

STEP B (9$\alpha$, 11$\beta$, 16$\alpha$)-21-(acetyloxy)-9-bromo-11-(formyloxy)-16,17-[(1-methylethylidene)bis(oxy)-$\Delta^{1,4}$-pregnadiene-3,20-dione 200 g of the product of Step A, 75 ml of isopropenyl acetate and 1 liter of acetone were mixed together at 20° C. under an inert gas and then 1 ml of perchloric acid at 55° Be was added. The mixture was refluxed for 3 hours, then cooled down to 20° C. and 80 ml of triethylamine were added. The reaction mixture was concentrated under reduced pressure at 30° C. and then the acetone was distilled off while keeping the volume constant by the addition of 600 ml of methanol. Then, 200 ml of water were added slowly at 20° C., followed by cooling down to 0° to +5° C. and the crystals were separated out, washed with a methanol-water mixture and dried to obtain 211.4 g of the expected product melting at 207.5° C.

NMR Spectrum (CDCl$_3$ MHz ppm) 18CH$_3$: 0.86 (s); 19CH$_3$: 1.24 (s); twinned diCH$_3$: 1.51–1.57 (s); CH$_3$CO: 2.17 (s); COCH$_2$—O: 4.74–4.97 (d); H$_{11}$: 5.93 (tl); H$_4$:6.09 (tl); H$_{16}$: 5.00 (d); H$_2$: 6.34 (dd); H$_1$: 6.84 (d); CHO: 8.13 (s).

STEP C (11$\beta$, 16$\alpha$)-11-(formyloxy)-16,17[(1-methylethylidene) -bis(oxy)]-21-(acetyloxy-$\Delta^{1,4}$-pregnadiene-3,20-dione 200 g of the product of Step B and 1 liter of tert-butanol were mixed together under an inert gas at 20° C. and the mixture was refluxed slowly. Then, 0.5 g of azobisisobutyronitrile was added and then over about one hour, 145.4 g of tributyltin hydride were added. Reflux was maintained for 3 hours and then the tert-butanol was distilled off while keeping the volume constant by the addition of 1.5 liters of a methylcyclohexane—cyclohexane mixture. The mixture was cooled down to about 3° C. over one hour and the crystals were filtered out, washed with a methylcyclohexane—cyclohexane mixture and dried to obtain 163.5 g of the expected product melting at 240.5° C.

NMR Spectrum (CDCl$_3$ MHz ppm) 18CH$_3$: 0.85 (s); 19CH$_3$: 1.32 (s); twinned dimethyl: 1.22 (s) and 1.45 (s); OCOCH$_3$: 2.17 (s); COCH$_2$—OCOCH$_3$: 4.71 (d, J=18) and 4.99 (d, J=18); H$_{16}$: 5.00 (d, J=3.5); H$_{11}$: 5.72; H$_4$: 6.05 (s); H$_2$: 6.30 (d,d); H$_1$: 6.95 (d); the other CH and CH$_2$: 1.15 to 2.6.

EXAMPLE 2

(11$\beta$, 16$\alpha$)-16,17-[butylidene-bis(oxy)]-$\Delta^{1,4}$-pregnadiene-11,21-diol-3,20-dione STEP A (11$\beta$, 16$\alpha$)-16,17-[butylidene-bis(oxy)]-11-(formyloxy)-21-(acetyloxy)-$\Delta^{1,4}$-pregnadiene-3,20-dione 200 g of the product of Example 1 and 1200 ml of methylene chloride were mixed together under an inert gas at ambient temperature. 90 ml of butanal were added to the mixture at 0°±1° C. and then, over about 5 minutes and while maintaining the temperature at 0°±1° C. 100 ml of 72% perchloric acid were added. The mixture was stirred for 2 hours 30 minutes at the same temperature and then was neutralized by the addition of 2 liters of a saturated aqueous solution of sodium bicarbonate. The mixture was stirred at 0°±2° C. for 30 minutes and then, 190 g of sodium metabisulfite were added. The mixture was stirred at 0°±2° C. for 30 minutes and then was reheated to ambient temperature and decanted. The aqueous phase was extracted with methylene chloride and the combined organic phases were washed with water, dried and treated with 20 g of activated charcoal. The methylene chloride was evaporated off while keeping the volume constant by adding a cyclohexane—methylcyclohexane mixture and the suspension was stirred for one hour at 0°±1° C. to obtain 200.4 g of the expected product which was used as is for the following step.

NMR Spectrum (CDCl$_3$ 300 MHz ppm) 18CH$_3$: 0.86 and 0.91; 19CH$_3$: 1.32 (s); CH$_3$ of butylidene: 0.92 (t) and 0.94 (t); OAc: 2.15 and 2.16 (s);

4.63 (.t) and 5.20 (t); H$_{16}$: 4.86 (d) and 5.14 (d); CO—CH$_2$—O—CO: 4.71 to 4.88; H$_{11}$: 5.71 (m); H$_4$:

6.04; H$_2$: 6.28 (resolved d,d); H$_1$: 6.94 (resolved d); OCH—O: 8.17 (s).

STEP B (11β, 16α)-16,17-[butylidene-bis(oxy)]-Δ$^{1,4}$-pregnadiene-11,21-diol-3,20-dione 190 g of the product of Step A and 1140 ml of dioxane were mixed together at ambient temperature under an inert gas and then the solvent was distilled off at 30° to 35° C. under 35 to 40 mm Hg until the water present was eliminated. A volume of about 1 liter was obtained in the reaction medium and after cooling down to 20° to 25° C., 950 ml of methanol were added, followed by cooling down to 10° C.±1° C. 92 ml of a 0.96M methanolic solution of potassium hydroxide were added. The mixture was stirred for one hour and then, still at 10° C.±1° C., 2 ml of acetic acid were added. The mixture was stirred for another 30 minutes followed by treating with 9.5 g of activated charcoal. The solution was poured slowly into 950 ml of water at about 65° C. under a pressure of 35 to 40 mm Hg while distilling at constant volume. Then, the suspension was cooled down and stirred for 2 hours at ambient temperature. The crystals were separated out, washed with water and dried to obtain 159.3 g of the expected product. The product was purified in 5 volumes of a mixture of water and methylisobutylketone (3/1), which was taken to about 60° C. with stirring for one hour, then cooled down to 20° C. for 2 hours. The crystals were separated out and washed with methylisobutylketone, then with water and dried to obtain 137.7 g of the expected producted with a specific rotation of [a]$^{25}_D$=103.3 (1% in CH$_2$Cl$_2$).

NMR Spectrum (CDCl$_3$ 300 MHz ppm) 18CH$_3$: 0.93 and 0.99 (s); 19CH$_3$: 1.46 (s); CH$_3$ of the butylidene: 0.92 (t) and 0.93 (t); CO—CH$_2$—O: 4.20 (d).and 4.63 (d), 4.27 (d) and 4.52 (d); H$_{11}$: 4.52 (m);

4.55 (t) and 5.17 (t); H$_{16}$: 4.90 (d) ; H$_4$: 6.03; H$_2$: 6.28 (resolved d,d); H$_1$: 7.30 (resolved d).

EXAMPLE 3

(11β, 16α)-16,17-[(1-methyl-ethylidene)-bis(oxy)-Δ$^{1,4}$-pregnadiene-11,21-diol-3,20-dione 140 g of the product of Example 1, 700 ml of methanol and 700 ml of dioxane were mixed together at ambient temperature and under an inert gas and after the mixture was cooled down to 10° C.±1° C., 33.5 ml of a 0.86M methanolic solution of potassium hydroxide were added over 5 minutes. The mixture was stirred at the same temperature for one hour and then 0.8 ml of acetic acid were added, followed by treating with 7 g of activated charcoal. The solution was then poured slowly into 700 ml of water at about 25° C. under a pressure of 50 to 60 nun Hg while distilling at constant volume. Once the addition is complete, 140 ml of water were added under the same conditions and the mixture was cooled to about 10° C. and stirred for one hour. The crystals were separated out, washed with water and dried to obtain 118 g of the expected product. The product was made into a paste while hot in 590 ml of ethanol and then was separated and dried. A new purification was carried out by pouring slowly a solution of 106 g of the product in 423 ml of dimethylformamide into 423 ml of water at 50° C. and after cooling to about +15° C., the crystals were separated and dried to obtain 103.6 g of the expected product melting at 281° C.

NMR Spectrum (CDCl$_3$ 300 MHz ppm) 18CH$_3$: 0.89 (s); 21OH: 3.11 (t, J=5 Hz); 21CH$_2$: 4.17 (dd, J=5 and 20 Hz); 4.67 (dd, J=5 and 20 Hz); H$_{11}$: 4.51 (m); H$_{16}$: 5.05 (d); H$_4$: 6.03 (s); H$_2$: 6.28 (d,d); H$_1$: 7.28 (d).

Various modifications of the products and processes of the invention may be made without departing from the spirit or scope thereof and it is to be understood that the invention is intended to be limited only as defined in the appended claims.

What we claim is:

1. A compound having a structural formula selected from the group consisting of

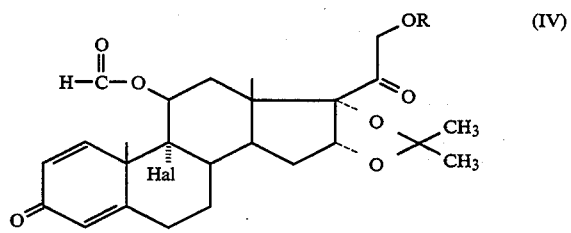

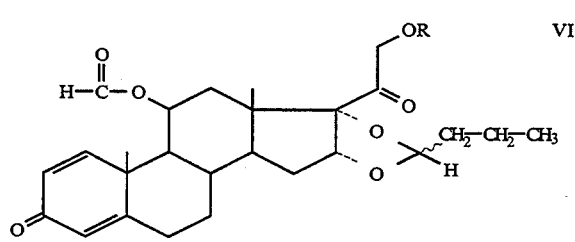

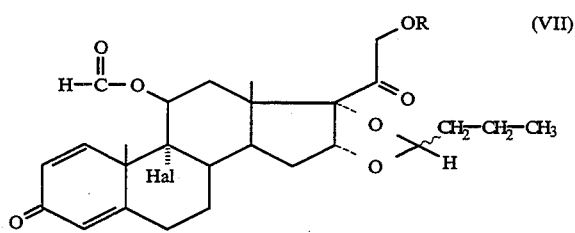

wherein R is selected from the group consisting of hydrogen, acyl of an organic carboxylic acid of 1 to 8 carbon atoms, allyloxycarbonyl, alkoxycarbonyl and aralkoxycarbonyl of up to 8 carbon atoms and a alkylsulfonyl and aralkylsulfonyul of up to 8 carbon atoms, and the wavy lines indicates the existence of 2 isomers.

* * * * *